(12) United States Patent
Shintaku et al.

(10) Patent No.: US 6,649,768 B1
(45) Date of Patent: Nov. 18, 2003

(54) PRODUCTION METHODS OF IMIDAZOLE COMPOUND AND SALT THEREOF AND INTERMEDIATES THEREFOR

(75) Inventors: Tetsuya Shintaku, Osaka (JP); Nobushige Itaya, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 10/309,961

(22) Filed: Dec. 4, 2002

(51) Int. Cl.[7] .................. C07D 401/04; C07D 213/04
(52) U.S. Cl. .................... 546/274.1; 546/315
(58) Field of Search ................ 546/274.1, 315

(56) References Cited

U.S. PATENT DOCUMENTS

| | | |
|---|---|---|
| 4,134,983 A | 1/1979 | Baldwin |
| 4,377,696 A | 3/1983 | Graf |
| 4,719,309 A | 1/1988 | Mesch |
| 4,853,383 A | 8/1989 | Baldwin et al. |
| 6,353,108 B1 | 3/2002 | Bouchet et al. |

FOREIGN PATENT DOCUMENTS

| | | |
|---|---|---|
| JP | 2002-348286 A | 12/2002 |
| WO | WO 00/02875 | 1/2000 |

OTHER PUBLICATIONS

Baldwin et al., "β–Adrenergic Blocking Agents with Acute Antihypertensive Activity," *Journal of Medicinal Chemistry*, 22 (6), 687–694 (1979).

Kirchhoff et al., "Automated Process Research and the Optimization of the Synthesis of 4(5)–(3–Pyridyl)imidazole," *Organic Process Research & Development*, 5 (1), 50–53 (2001).

Chemical Abstracts, 80, p. 389, 82801a (1974).

*Primary Examiner*—Zinna Northington Davis
(74) *Attorney, Agent, or Firm*—Leydig, Voit & Mayer, Ltd.

(57) ABSTRACT

A production method including a step for converting a halogen compound of the formula (6) or a salt thereof to a glyoxal compound of the formula (2) or a salt thereof in dimethyl sulfoxide, and a step for reacting the glyoxal compound of the formula (2) or a salt thereof obtained in the previous step with ammonia and an aldehyde compound of the formula (3) or a salt thereof can conveniently produce an imidazole compound of the formula (1) or a salt thereof. The imidazole compound is a synthetic intermediate for a compound useful as pharmaceutical agents and agricultural chemicals. The production method is suitable for industrial scale production.

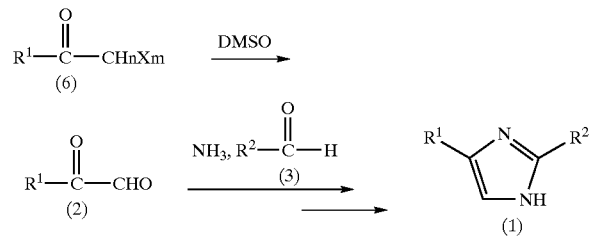

is wherein each symbol is as defined in the specification.

4 Claims, No Drawings

PRODUCTION METHODS OF IMIDAZOLE COMPOUND AND SALT THEREOF AND INTERMEDIATES THEREFOR

The present invention relates to a production method of an imidazole compound or a salt thereof, which is a synthetic intermediate for a compound useful as pharmaceutical agents and agricultural chemicals, and a novel intermediate useful for the production of the imidazole compound.

BACKGROUND ART

Imidazole compound is a synthetic intermediate for a compound useful as pharmaceutical agents and agricultural chemicals. For example, 3-(4-imidazolyl)pyridine is useful as a synthetic intermediate for telithromycin useful as antibiotics.

There have been developed various synthetic methods of imidazole compounds including 3-(4-imidazolyl)pyridine useful as such synthetic intermediate. In WO00/02875, for example, 3-(4-imidazolyl)pyridine is produced from 3-acetylpyridine as a starting material through oximation, tosylation, azirine formation, ring opening in acidic alcohol and ring closure to imidazole in formamide. However, such production methods are complicated and unsuitable as industrial production methods. Therefore, the development of a method for conveniently producing 3-(4-imidazolyl)pyridine and a salt thereof, which is suitable for industrial scale production, is desired.

It is therefore an object of the present invention to provide 1) a method capable of conveniently producing 3-(4-imidazolyl)pyridine and a salt thereof, which is suitable for industrial scale production, and 2) a novel intermediate and a salt thereof for an imidazole compound.

DISCLOSURE OF THE INVENTION

As a result of the intensive studies done by the present inventors in an attempt to achieve the above-mentioned object, they have found that an imidazole compound of the following formula (1) can be conveniently produced via the following step 2 and step 3, and that this method is suitable for industrial scale production, which resulted in the completion of the present invention.

The present inventors have further found a method for producing a glyoxal compound of the following formula (2) (hereinafter to be also referred to as glyoxal compound (2)), which comprises halogenating a carbonyl compound of the following formula (5) (hereinafter to be also referred to as carbonyl compound (5)) to give a halogen compound of the following formula (6) (hereinafter to be also referred to as halogen compound (6)) and converting a —CHnXm group of the halogen compound (6) to an aldehyde group, and completed the present invention.

Accordingly, the present invention relates to the following (1) to (5).

(1) A production method of an imidazole compound of the formula (1)

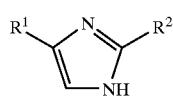
(1)

wherein
R$^1$ is an aryl group optionally having substituent(s) or a heterocyclic residue optionally having substituent(s); and R$^2$ is a hydrogen atom, an alkyl group optionally having substituent(s), an unsaturated alkyl group optionally having substituent(s), a cycloalkyl group optionally having substituent(s), an aralkyl group optionally having substituent(a), an arylalkenyl group optionally having substituent(s), an aryl-cyclic hydrocarbon group optionally having substituent(s), an aryl group optionally having substituent(s) or a heterocyclic residue optionally having substituent(s) (hereinafter to be also referred to as imidazole compound (1)), or a salt thereof, which comprises step 2: a step for converting, in dimethyl sulfoxide, a halogen compound of the formula (6)

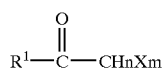
(6)

wherein R$^1$ is as defined above, X is a chlorine atom or a bromine atom, m and n are each an integer of 1 or 2, and m+n is 3, or a salt thereof, to a glyoxal compound of the formula (2)

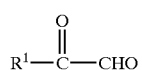
(2)

wherein R$^1$ is as defined above, or a salt thereof, and step 3: a step for reacting the glyoxal compound (2) or a salt thereof obtained in step 2 with ammonia and an aldehyde compound of the formula (3)

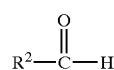
(3)

wherein R$^2$ is as defined above (hereinafter to be also referred to as aldehyde compound (3)) or a salt thereof.

(2) The production method of the above-mentioned (1), which further comprises step 1: a step for obtaining a halogen compound (6) or a salt thereof by chlorination or bromination of a carbonyl compound of the formula (5)

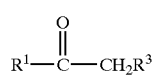
(5)

wherein R$^1$ is an aryl group optionally having substituent(s) or a heterocyclic residue optionally having substituent(s), and R$^3$ is a hydrogen atom or an alkoxycarbonyl group, or a salt thereof.

(3) The production method of the above-mentioned (1) or (2), wherein, in step 2, a base is added after confirmation of the start of the conversion of the halogen compound (6) or a salt thereof to the glyoxal compound (2) or a salt thereof.

(4) The production method of any of the above-mentioned (1) to (3), wherein, R$^1$ is a 3-pyridyl group and R$^2$ is a hydrogen atom.

(5) (3-Pyridyl)glyoxal, a solvate thereof or a salt thereof.

EMBODIMENT OF THE INVENTION

The definition of each symbol is given in the following.

The alkyl group in the present invention is preferably a linear or branched alkyl group having 1 to 24 carbon atoms, such as methyl, ethyl, propyl, isopropyl, butyl, isobutyl, sec-butyl, tert-butyl, pentyl, hexyl, heptyl, octyl, nonyl, decyl, dodecyl, undecyl and the like.

The unsaturated alkyl group in the present invention is preferably a linear or branched unsaturated alkyl group having 2 to 24 carbon atoms, such as alkenyl (e.g., vinyl, 1-propenyl, 2-propenyl, isopropenyl, butenyl, pentenyl, hexenyl, heptenyl, octenyl, nonenyl, decenyl, dodecenyl, undecenyl and the like); and alkynyl (e.g., ethynyl, propynyl, butynyl, pentynyl, hexynyl, heptynyl, octynyl, nonynyl, decynyl, dodecynyl, undecynyl and the like).

The cycloalkyl group in the present invention is preferably a saturated or unsaturated cycloalkyl having 3 to 6 carbon atoms, such as cyclopropyl, cyclohexyl and the like.

The aryl group in the present invention is exemplified by phenyl, naphthyl, anthranyl and the like.

The aralkyl group in the present invention is preferably an aralkyl group having 7 to 24 carbon atoms, wherein the alkyl moiety is linear or branched. Examples thereof include benzyl, phenethyl, naphthylmethyl and the like.

The arylalkenyl group in the present invention preferably has 8 to 24 carbon atoms, wherein the aryl moiety is as defined for the above-mentioned aryl and the alkenyl moiety is linear or branched. Examples thereof include phenylethenyl, phenylpropenyl, phenylbutenyl, naphthylethenyl, naphthylpropenyl and the like.

The aryl-cyclic hydrocarbon group in the present invention preferably has 9 to 24 carbon atoms, wherein the aryl moiety is as defined for the above-mentioned aryl and the cyclic hydrocarbon moiety is saturated or unsaturated. Examples thereof include phenylcyclopropyl, phenylcyclopentyl, phenylcyclohexyl, naphthylcyclopropyl, naphthylcyclopentyl, naphthylcyclohexyl and the like.

The heterocyclic residue in the present invention is preferably an unsaturated 5- or 6-membered ring having 1 or more hetero atoms (e.g., nitrogen atom, oxygen atom, sulfur atom and the like). Examples thereof include furyl group, thienyl group, pyridyl group, pyrimidinyl group, quinolyl group and the like.

The alkoxycarbonyl group in the present invention is preferably a linear or branched alkoxycarbonyl group having 2 to 8 carbon atoms. Examples thereof include methoxycarbonyl, ethoxycarbonyl, propoxycarbonyl, butoxycarbonyl, isobutoxycarbonyl, sec-butoxycarbonyl, tert-butoxycarbonyl, pentyloxycarbonyl, hexyloxycarbonyl, heptyloxycarbonyl and the like, with preference given to methoxycarbonyl and ethoxycarbonyl.

The aryl group and heterocyclic residue for $R^1$ and alkyl group, unsaturated alkyl group, cycloalkyl group, aralkyl group, aryl group, arylalkenyl group, aryl-cyclic hydrocarbon group and heterocyclic residue for $R^2$ are optionally substituted with 1 or more substituents. Examples of the substituent include linear or branched alkyl group having 1 to 12 carbon atoms (e.g., methyl, ethyl, propyl, isopropyl, butyl, isobutyl, sec-butyl, tert-butyl, pentyl, hexyl, heptyl, octyl, nonyl, decyl, dodecyl and the like), unsaturated alkyl group, halogen atom (fluorine atom, chlorine atom, bromine atom, iodine atom), linear or branched alkoxy group having 1 to 12 carbon atoms (e.g., methoxy, ethoxy, propoxy, isopropoxy, butoxy, isobutoxy, sec-butoxy, tert-butoxy, pentyloxy, hexyloxy, heptyloxy, octyloxy, nonyloxy, decyloxy, dodecyloxy and the like), carboxyl group, heterocyclic residue and the like.

The imidazole compound (1) in the present invention is exemplified by 3-(4-imidazolyl)pyridine and the like.

The glyoxal compound (2) is exemplified by a novel compound, (3-pyridyl)glyoxal, which is a useful synthetic intermediate for pharmaceutical products. This compound can be obtained by converting the dibromomethyl group of 3-(dibromoacetyl)pyridine or a hydrobromide thereof to an aldehyde group in dimethyl sulfoxide.

The aldehyde compound (3) is exemplified by formaldehyde, acetaldehyde, propionaldehyde, benzaldehyde and the like, with preference given to formaldehyde.

The carbonyl compound (5) is preferably 3-(3-pyridyl)-3-oxopropionic acid ethyl ester or 3-acetylpyridine.

The halogen compound (6) is exemplified by a novel compound, 3-(dibromoacetyl)pyridine, and a hydrobromide thereof, which are useful synthetic intermediates for pharmaceutical products.

Each compound of the present invention includes an isomer, an optically active form and a mixture thereof when each compound of the present invention has an asymmetric carbon atom, and a solvate (e.g., hydrate) when a solvate can be formed.

The salt of each compound of the present invention is exemplified by, a salt with a base (e.g., salt with triethylamine arid the like) when it has an acidic group, and a salt with an acid (e.g., hydrobromide, hydrochloride, sulfate, oxalate, mesylate, tosylate and the like) when it has a basic group.

The steps 1–3 are explained in order in the following. Each compound in the explanation may be an isomer, an optically active form or a salt as long as it is not particularly limited, and each compound does not show a free form but encompasses any form possibly taken. The compound obtained in each step can be used in the next step without isolation or purification.

Step 1

In Step 1, carbonyl compound (5) is chlorinated or brominated to give halogen compound (6). Specifically, carbonyl compound (5) and a reaction solvent are stirred, to which a chlorinating agent or a brominating agent is added, preferably by dropwise addition, and further stirred. The chlorinating agent or brominating agent may be added at room temperature to 100° C.

When carbonyl compound (5) wherein $R^3$ is an alkoxycarbonyl group is used, the chlorinating agent or brominating agent is preferably added to a solution of carbonyl compound (5) in a reaction solvent. For example, carbonyl compound (5) is added to a reaction solvent and the obtained mixture is stirred, to which a chlorinating agent or brominating agent is added, preferably by dropwise addition, and the mixture is further stirred.

The reaction solvent in step 1 is exemplified by water, aqueous HBr solution and the like, preferably aqueous HBr solution The amount of the reaction solvent to be used is not particularly limited as long as the reaction mixture can be stirred.

The chlorinating agent or brominating agent to be used in step 1 is exemplified by brominating agents such as bromine, N-bromosuccinimide (NBS), Dibromantin (1,3-dibromo-5,5-dimethylhydantoin) and the like; and chlorinating agents such as chlorine, sulfuryl chloride and the like (under anhydrous conditions), with preference given to bromine. The amount of the chlorinating agent or brominating agent to be used varies depending on whether the desired halogen compound is monohalogeno compound or dihalogeno compound. When it is a monohalogeno compound, the amount is generally 1–1.5 mol, preferably 1–1.2 molt relative to 1 mol of carbonyl compound (5), and when it is dihalogeno compound, the amount is generally 2–4 mol, preferably 2–2.5 mol, relative to 1 mol of carbonyl compound (5).

While step 1 depends on the kind of carbonyl compound (5) and the like, it is carried out at ambient temperature to 80° C., wherein it is preferably 40–60° C. when a monohalogeno compound is desired, and preferably 50–70° C. when a dihalogeno compound is desired.

The halogen compound (6) can be isolated and purified by a conventional method. For example, halogen compound (6) can be isolated by cooling and filtering the reaction mixture, and can be purified by washing the resulting isolate.

Step 2

In step 2, halogen compound (6) is converted to glyoxal compound (2) in dimethyl sulfoxide (DMSO), by specifically, for example, stirring halogen compound (6) and DMSO.

The present inventors have surprisingly found that, in step 2, addition of a base after confirmation of the start of the conversion of halogen compound (6) to glyoxal compound (2) in DMSO increases the yield of glyoxal compound (2). The yield of glyoxal compound (2) does not increase by the addition of base before the start of this reaction. The start of the reaction can be confirmed by high-performance liquid chromatography (HPLC), lower pH and the like.

DMSO in step 2 can be used in an amount sufficient to make the reaction mixture stirrable. For example, it is used in an amount of generally 1.5–3 ml, preferably 1.7–2.2 ml, relative to 1 g of halogen compound (6).

The base to be used in step 2 is exemplified by alkali metal compound (e.g., carbonate such as sodium carbonate, potassium carbonate, lithium carbonate and the like; hydroxide such as sodium hydroxide and the like, and the like), preferably sodium carbonate. The amount of the base to be used is generally 0.45–0.55 mol, preferably 0.47–0.52 mol, relative to 1 mol of halogen compound (6).

While step 2 depends on the kind of halogen compound (6) 15 and the like, stirring is generally done at 30–40° C. for 4–5 hr. When a base is added, further stirring after addition at 20–30° C. is preferable. The end of step 2 can be confirmed by HPLC and the like.

The glyoxal compound (2) can be isolated and purified by a conventional method. For example, glyoxal compound (2) can be isolated by applying preparative TLC and the like, and may be purified by applying the isolate to preparative HPLC. The glyoxal compound (2) can be generally obtained as a hydrate, and can be converted to an anhydrate by a conventional method.

The halogen compound (6), which is a starting material of step 2, can be produced by a known method. The above-mentioned step 1 is preferable as the production method of halogen compound (6), because this method can be conducted at an industrial scale.

Step 3

In step 3, imidazole compound (1) is obtained by reacting glyoxal compound (2) obtained in step 2 with ammonia and aldehyde compound (3). Specifically, for example, ammonia, aldehyde compound (3) and a reaction solvent are stirred, to which a solution of glyoxal compound (2) in a reaction solvent is added, preferably by dropwise addition. The glyoxal compound (2) to be used as a starting material may be non-solvate or solvate (particularly hydrate).

In step 3, glyoxal compound (2) is reacted with ammonia and aldehyde compound (3) to give a compound of the formula (4)

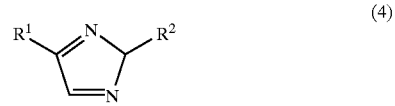

wherein each symbol is as defined above (hereinafter to be referred to as compound (4)), wherein the formation of compound (4) and an equilibrium reaction of compound (4) and imidazole compound (1) are considered to occur simultaneously. The imidazole compound (1) is thermodynamically stabler than compound (4), as a result of which imidazole compound (1) is considered to be obtained.

The reaction solvent to be used in step 3 is exemplified by methanol, water and a mixed solvent thereof and the like, preferably water and aqueous methanol, more preferably water. The amount of the reaction solvent to be used is not particularly limited as long as it is sufficient to make the reaction mixture stirrable.

As ammonia, aqueous ammonia is preferable in view of easy handling. Water contained in aqueous ammonia can be used as a reaction solvent. The amount of ammonia to be used is generally 3–50 mol, preferably 10–40 mol, relative to 1 mol of halogen compound (6) used in step 2, when step 3 is conducted after step 2 without isolation of the resulting product.

The amount of aldehyde compound (3) to be used is generally 1.2–20 mol, preferably 1.5–15 mol, relative to 1 mol of halogen compound (6) used in step 2, when step 3 is conducted after step 2 without isolation of the resulting product.

Step 3 is conducted generally at 0–40° C., preferably 10–30° C., and heated to 100° C. where necessary, though subject to change depending on the kind of halogen compound (6) and aldehyde compound (3) used in step 2 and the like. The end of the reaction can be confirmed by HPLC and the like.

The imidazole compound (1) can be isolated and purified by a conventional method. The imidazole compound (1) can be isolated by converting to a salt with an acid by, for example, concentrating the reaction mixture and re-dissolving the concentrate in a solvent. washing of the isolate affords purification. The salt can be converted to a free form by a conventional method.

When $R^1$ is a 3-pyridyl group and $R^2$ is a hydrogen atom, 3-(4-imidazolyl)pyridine can be obtained as imidazole compound (1) by the method of the present invention. The obtained 3-(4-imidazolyl)pyridine (imidazole compound (1)) can be introduced into telithromycin useful as a pharmaceutical agent, according to WO00/02875.

EXAMPLES

The present invention is explained in detail in the following by referring to Examples, which are not to be construed as limitative.

Example 1

Synthesis of 3-(Dibromoacetyl)pyridine Hydrobromide 3-(3-Pyridyl)-3-oxopropionic acid ethyl ester (1.95 g, 10.2 mmol) was added dropwise to 47% aqueous HBr solution (3.86 g) under ice-cooling. Bromine (2.2 g, 1.2 equivalent amount relative to 3-(3-pyridyl)-3-oxopropionic acid ethyl ester) was added dropwise at not more than 10° C. After stirring for 30 min, iced-water bath was removed and water (2 ml) and 47% aqueous HBr solution (4 ml) were added. The mixture was stirred at room temperature for 30 min. Furthermore, bromine (2.2 g, 1.2 equivalent amount relative to 3-(3-pyridyl)-3-oxopropionic acid ethyl ester) was added dropwise and the mixture was stirred at 65–70° C. After cooling to room temperature, the reaction mixture was filtrated to give 3.73 g of the titled compound (yield 95.2%).

Example 2

Synthesis of 3-(Dibromoacetyl)pyridine Hydrobromide

3-Acetylpyridine (50 g, 0.41 mol), 47% aqueous HBr solution (106.6 g, 1.5 equivalent amount relative to 3-acetylpyridine) and water (80 ml) were charged in a reaction vessel and the mixture was stirred at 55–60° C. Bromine (135.2 g, 2.05 equivalent amount relative to 3-acetylpyridine) was added dropwise and the mixture was stirred for one more hour. The mixture was cooled to 5° C. under ice-cooling, and filtered to give 146.7 g of the titled compound as crystals (yield 99.0%).

$^1$H-NMR(400 MHz, DMSO-d$_6$) δ 9.43(s, 1H), 9.04(dd, J=4.9, 1.0 Hz, 1H), 8.86–8.84(m, 1H), 8.02–7.99(m, 1H), 7.94(d, J=1.0 Hz, 1H). FT-IR(KBr)ν$_{max}$1712 cm$^{-1}$. elemental analysis :C$_7$H$_6$NOBr$_3$; Found C, 23.36; H, 1.68; Br, 66.62; N, 3.89. Calculated C, 23.3; H,1.7; Br, 66.61; N, 4.0.

Example 3

Synthesis of 3-(4-Imidazolyl)pyridine 3-(Dibromoacetyl)pyridine hydrobromide (3.00 g, 8.34 mmol) and DMSO (6 ml) were added in a reaction vessel and the mixture was stirred at 33–36° C. for 4 hr. As a result of the confirmation by HPLC, an area percentage of (3-pyridyl)glyoxal was 33.8%. After cooling to 20° C., Na$_2$CO$_3$ (0.44 g, 4.2 mmol) was added and the mixture was stirred at room temperature for 2 days (the reaction mixture A). As a result of the HPLC analysis, an area percentage of (3-pyridyl)glyoxal was 71.2%.

Separately, formaldehyde (6.77 g, 0.083 mol) was added dropwise 28% aqueous ammonia (15.21 g, 0.25 mol) under ice-cooling at not more than 10° C. to prepare reaction mixture B. The reaction mixture A was diluted with H$_2$O (4 ml) and the dilute reaction mixture A was added dropwise to the reaction mixture B at −3 to 2° C. The mixture was stirred overnight at 20–30° C. to give 3-(4-imidazolyl)pyridine. From the LC analysis, the yield thereof was 59.3%.

$^1$H-NMR(400 MHz, CDCl$_3$) δ 8.99 (d, J=2.0 Hz, 1H), 8.43(dd, J=4.9, 1.5 Hz, 1H), 8.05(dt, J=8.3, 2.0 Hz, 1H), 7.77(d, J=1.0 Hz, 1H), 7.43(d, J=1.0 Hz, 1H), 7.29(dd, J=7.8, 4.9 Hz, 1H). melting point: 117.0–118.3° C.

Example 4

3-(Dibromoacetyl)pyridine hydrobromide (1.5 g, 4.17 mmol) and DMSO-d$_6$ (4 ml) were added to a reaction vessel, and the mixture was stirred at 35–40° C. for 4 hr. A portion thereof was taken and subjected to $^{13}$C-NMR measurement. As a result, formation of (3-pyridyl)glyoxal (hydrate) was confirmed.

$^{13}$C-NMR(100 MHz, DMSO-d$_6$): δ=192.8(CO), 90.3 (CHO)ppm.

Industrial Applicability

According to the present invention, an imidazole compound which is a synthetic intermediate for a compound useful as pharmaceutical agents and agricultural chemicals can be produced conveniently. This method is suitable for industrial scale production. Moreover, the present invention provides a novel intermediate useful for the production of the imidazole compound.

What is claimed is:

1. A production method of an imidazole compound of the formula (1)

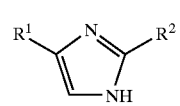

(1)

wherein

R$^1$ is 3-pyridyl; and

R$^2$ is a hydrogen atom, an alkyl group optionally having substituent(s), an unsaturated alkyl group optionally having substituent(s), a cycloalkyl group optionally having substituent(s), an aralkyl group optionally having substituent(s), an arylalkenyl group optionally having substituent(s), an aryl-cyclic hydrocarbon group optionally having substituent(s), an aryl group optionally having substituent(s) or a heterocyclic residue optionally having substituent(s), or a salt thereof, which comprises (a) converting, in dimethyl sulfoxide, a halogen compound of the formula (6)

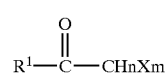

(6)

wherein R$^1$ is as defined above, X is a chlorine atom or a bromine atom, m and n are each an integer of 1 or 2, and m+n is 3, or a salt thereof, to a glyoxal compound of the formula (2)

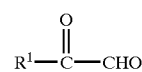

(2)

wherein R$^1$ is as defined above, or a salt thereof, and (b) reacting the glyoxal compound of the formula (2) or a salt thereof obtained in step (a) with ammonia and an aldehyde compound of the formula (3)

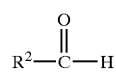

(3)

wherein R$^2$ is as defined above, or a salt thereof.

2. The production method of claim 1, wherein the halogen compound of the formula (6) or a salt thereof is obtained by chlorination or bromination of a carbonyl compound of the formula (5)

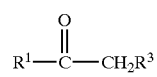
(5)
wherein R¹ is 3-pyridyl, and R³ is a hydrogen atom or an alkoxycarbonyl group,
or a salt thereof.
3. The production method of claim 1, wherein, in step (a), a base is added after the halogen compound of the formula (6) or a salt thereof begins to convert to the glyoxal compound of the formula (2) or a salt thereof.
4. The production method of claim 1, wherein, $R^2$ is a hydrogen atom.
* * * * *